United States Patent [19]

Gall

[11] Patent Number: 4,577,020

[45] **Date of Patent: * Mar. 18, 1986**

[54] AMINOALKYL AND AMINOALKENYL TRIAZOLES AS ANTI-PSYCHOTIC AGENTS

[75] Inventor: Martin Gall, Kalamazoo, Mich.

[73] Assignee: The Upjohn Company, Kalamazoo, Mich.

[ * ] Notice: The portion of the term of this patent subsequent to Jul. 6, 1999 has been disclaimed.

[21] Appl. No.: 460,723

[22] Filed: Jan. 25, 1983

[51] Int. Cl.[4] .................. C07D 403/06; C07D 249/08; A61K 31/495; A61K 31/41

[52] U.S. Cl. .................................... 544/366; 546/208; 546/210; 548/269

[58] Field of Search ........................ 544/366; 542/425; 546/208, 210; 548/269

[56] References Cited

U.S. PATENT DOCUMENTS

| | | | |
|---|---|---|---|
| 3,910,943 | 10/1975 | Gall | 544/366 |
| 3,969,366 | 7/1976 | Wade et al. | 544/366 |
| 4,338,453 | 7/1982 | Gall | 548/263 |
| 4,404,382 | 9/1983 | Gall | 544/366 |
| 4,408,049 | 10/1983 | Gall | 544/366 |

*Primary Examiner*—George F. Lesmes
*Assistant Examiner*—S. A. Gibson
*Attorney, Agent, or Firm*—Lawrence T. Welch

[57] ABSTRACT

The present invention provides certain aminoalkyl and aminoalkenyl triazoles which are useful as anti-psychotics. Certain of these aminoalkyl triazoles were previously known as anti-allergy agents.

5 Claims, No Drawings

AMINOALKYL AND AMINOALKENYL TRIAZOLES AS ANTI-PSYCHOTIC AGENTS

BACKGROUND OF THE INVENTION

The present invention relates to novel compositions of matter. The present invention also relates to a new use for some old compounds. More particularly, the present invention relates to certain aminoalkyl or aminoalkenyl triazoles which are useful as anti-psychotic agents. Some of these compounds are also useful as analgesics.

Anti-psychotic or neuroleptic drugs are those used to treat the most severe psychiatric illnesses, the psychoses. The psychoses are a class of psychiatric diseases in which there is not only a marked impairment of an individuals behavior but also a serious inability of those afflicted to think coherently, to comprehend reality, or to gain insight into their own abnormality. These conditions often include delusions and hallucinations. Psychotic disorders include organic conditions which are typically associated with toxic, metabolic, or neuropathologic changes and are characterized by confusion, disorientation, and memory disturbances as well as behavioral disorganization and idiopathic (or functional) disorders for which underlying causes remain completely obscure. These latter disorders are characterized by the retention of orientation and memory in the presence of severely disordered emotion, thought, and behavior. Those primary disorders characterized by abnormal emotion or mood are called manic depressive disorders. The class of idiopathic psychoses characterized mainly by disordered thinking and emotional withdrawal, and often associated with paranoid delusions and auditory hallucinations, are called schizophrenia. The psychoses can vary in severity and they present a variety of specific symptom clusters. In addition, there are disorders marked by more or less isolated delusions. These latter disorders are sometimes referred to in a separate category of illness called paranoia. For a general discussion of psychoses, see, e.g., Goodman and Gilman, The Pharmacological Basis of Therapeutics, 391 (1980).

Several classes of drugs have been used for symptomatic treatment of psychoses. They are most often used in the treatment of schizophrenia, organic psychoses, and the manic phase of manic depressive illness. These classes of drugs include compounds such as the phenothiazines, the thioxanthenes, the dibenzodiazepines and dibenzoxazepines, the butyrophenones, the diphenylbutylpiperidines, the indolones and other heterocyclic compounds, and the rauwolfia alkaloids and related synthetic heterocyclic amine-depleting agents. Chlorpromazine is commonly used as a prototype for the group of anti-psychotic drugs. The chemical name for this compound is 2-chloro-N,N-dimethyl-10H-phenothiazine-10-propanamine. Many anti-psychotic drugs have sedative effects, as well as anti-anxiety effects. However, these antipsychotic compounds are not generally used for such purposes, because of their neurological and autonomic side effects. The term neuroleptic is used to define this class of drugs based on the observation of the effects of these drugs in humans. These drugs suppress spontaneous movements and complex behavior, while spinal reflexes and unconditioned nociceptive-avoidance behaviors remain intact. In humans, these drugs cause a striking loss of initiative, disinterest in the environment, diminished emotional responsiveness and limited range of affect. While initially there might be some slowness in response to external stimuli and drowsiness, subjects are generally easily aroused, capable of giving appropriate answers to direct questions, and seem to have their intellectual function intact. There is no ataxia, incoordination, or dysarthria. For a discussion of antipsychotic drugs which are currently used, see Goodman and Gilman, supra, at 397.

While the use of anti-psychotic or neuroleptic drugs has achieved some success, there is a need for an anti-psychotic drug which lacks the catalepsy and muscle rigidity or extra pyramidal side effects seen in humans given typical neuroleptics and which does not produce the late onset dyskinesia typically observed in patients chronically treated with neuroleptics.

PRIOR ART

Certain 1,2,4-triazoles are disclosed in U.S. Pat. No. 4,338,453. These compounds are disclosed as being useful for treatment of allergies and anaphylactic reactions. Additionally, some of these compounds are also useful in the treatment hypertension. A large number of antipsychotic agents are known, as stated above. However, these compounds have structures quite dissimilar to the compounds disclosed herein.

SUMMARY OF THE INVENTION

The present invention particularly provides:

(1) a compound of the Formula I, or an enantiomer or steroisomer thereof, wherein $R_4$ is
(a) hydrogen,
(b) $(C_1-C_3)$alkyl,
(c) $-CH_2OH$,
(d) $-CH_2OCOCH_3$
(e) $-S(O)_qCH_3$,
(f) $-SCH_2CH_3$, or
(g) $-R_{15}$;

wherein $R_5$, $R_{15}$, and $R_{25}$ are the same or different and are
(a) phenyl substituted by zero to 2 chloro, fluoro, bromo, alkyl of from one to 3 carbon atoms, nitro, or alkoxy of from one to 3 carbon atoms, or
(b) phenyl substituted by one trifluoromethyl and zero to one of the previous phenyl substituents;

wherein $W_1$ is
(a) cis—$C(R_3)=CH-CH_2NR_1R_2$,
(b) trans—$C(R_3)=CH-CH_2NR_1R_2$,
(c) $-C(CH_3)(OR_{14})-CH_2-CH_2NR_1R_2$,
(d) a substituent of the Formula III,
(e) a substituent of the Formula IV;

wherein $-NR_1R_2$ is
(a) $-N(CH_3)-CH_2(CH_2)_m-R_{25}$,
(b) $-NH-CH_2(CH_2)_mR_{25}$,
(c) a substituent of the Formula V,
(d) a substituent of the Formula VI,
(e) a substituent of the Formula VII, or
(f) $-N(CH_3)-(CH_2)_3-CH(R_{51})_2$;

wherein $R_{14}$ is
(a) hydrogen,
(b) $-COCH_3$, or
(c) $-COCH_2CH_3$;

wherein $R_{51}$ is
(a) phenyl,
(b) p-fluorophenyl, or
(c) p-chlorophenyl;

wherein $R_3$ is (a) hydrogen, or (b) methyl;

wherein the dotted line represents a single or double bond;

wherein m is an integer of from one to 2, inclusive;

wherein n is an integer of from zero to 3, inclusive; and wherein q is an integer of from zero to 2, inclusive; and (2) a method for the treatment of psychosis in a human suffering from or susceptible to said psychosis comprising systemically administering to said human an amount effective to treat the psychosis of a compound of the Formula II, or an enantiomer or stereoisomer thereof, wherein $R_4$ is (a) hydrogen, (b) $(C_1-C_3)$alkyl, (c) $-CH_2OH$, (d) $-CH_2OCOCH_3$ (e) $-S(O)_qCH_3$, (f) $-SCH_2CH_3$, or (g) $-R_{15}$;

wherein $R_5$, $R_{15}$, and $R_{25}$ are the same or different and are (a) phenyl substituted by zero to 2 chloro, fluoro, bromo, $(C_1-C_3)$alkyl, nitro, or $(C_1-C_3)$alkoxy, or (b) phenyl substituted by one trifluoromethyl and zero to one of the previous phenyl substituents;

wherein $W_2$ is (a) $-CH(R_3)-CH_2-CH_2-NR_1R_2$, (b) cis$-C(R_3)=CH-CH_2NR_1R_2$, (c) trans$-C(R_3)=CH-CH_2NR_1R_2$, (d) $-C(R_3)(OR_{14})-CH_2NR_1R_2$, (e) $-C(R_3)(OR_{14})-CH_2-CH_2NR_1R_2$, (f) a substituent of the Formula III, or (g) a substituent of the Formula IV;

wherein $-NR_1R_2$ is (a) $-N(CH_3)-CH_2(CH_2)_m-R_{25}$, (b) $-NH-CH_2(CH_2)_mR_{25}$, (c) a substituent of the Formula V, (d) a substituent of the Formula VI, (e) a substituent of the Formula VII, or (f) $-N(CH_3)-(CH_2)_3-CH(R_{51})_2$;

wherein $R_{51}$ is (a) phenyl, (b) p-fluorophenyl, or (c) p-chlorophenyl;

wherein $R_3$ is (a) hydrogen, or (b) methyl;

wherein $R_{14}$ is (a) hydrogen, (b) $-COCH_3$, or (c) $-COCH_2CH_3$;

wherein the dotted line represents a single or double bond;

wherein m is an integer of from one to 2, inclusive;

wherein n is an integer of from zero to 3, inclusive; and wherein q is an integer of from zero to 2, inclusive.

Certain enantiomers and stereoisomers are within the scope of Formulas I and II. Thus, when $W_1$ is definitions (a), (b), or (c) and $R_3$ is other than hydrogen, certain enantiomers are possible. Similarly, when $R_4$ is $-S(O)_qCH_3$, certain stereoisomers are possible. All of these enantiomers and stereoisomers are within the scope of this invention.

Compounds of the present invention have been evaluated in standard laboratory tests which demonstrate anti-psychotic activity. Thus, compounds of the present invention have been found to be active in both in vivo and in vitro $^3H$ Spiroperidol binding assays in the mouse, which assays demonstrate antipsychotic activity. For a discussion of binding assays, see, e.g., Pert, et al., Proc. Natl. Acad. Soc. USA, 70:2243 (1973) and Terenius, Acta Pharmac. Tox. 33:377 (1973). Thus, compounds of the present invention have been tested and found active in one or more of the following standard laboratory tests, which tests demonstrate antipsychotic activity:

A. Body temperature and apomorphine cage climbing antagonism

The same mice are used for the two tests. A group of 4 mice are injected intraperitoneally (I.P.) with the test compound. At the end of 45 minutes, the abdominal temperature is measured with a thermister probe. A control group of 4 mice are treated with the vehicle and the temperature is similarly taken. A compound is considered hypothermic or hyperthermic if the mean temperature of the treated group deviates more than 3.5 degree fahrenheit from the mean temperature of the parallel control group.

Immediately after the temperature measurement, apomorphine hydrochloride is injected I.P. at a dose of 2.5 mg/kg and the 4 mice in a group are placed on the floor of a wire cage (5"×5"×12"). The mice are observed between 5–10 minutes after apomorphine injection. During this time, mice that have climbed the walls more than half-way to the top (6") are removed from the cage. A compound is considered an antagonist of apomorphine if 2 or more animals remain in the cage at the end of 10 minutes.

B. Protection against d-amphetamine aggregation toxicity

A group of 4 mice are pretreated 1 hr. prior with test compound by I.P. injection. They are then injected additionally with d-amphetamine sulfate at 20 mg/kg I.P. The group of mice are then placed on a 1000 ml glass beaker with wood shavings at the bottom and covered with a wire-mesh. The beakers are wrapped with white paper around the side (to reduce transparency) and are placed on a counter top with normal room illumination. Deaths in the group are counted at the end of 2 hours. A compound is active if no more than one death occurs in the group.

C. In vitro spiroperidol binding assay

The homogenate is prepared by homogenizing a whole rat brain in 10 ml of 0.05M THAM—CHl, pH 7.4, using a Brinkman PT10 Polytron at setting 7 for 30 seconds, and centrifuging at 30,000 g for 10 minutes. The supernatant is discarded, the pellet resuspended in 10 ml buffer using the polytron at setting 7 for 10 seconds and the centrifugation repeated. The pellet is resuspended and diluted to 100 times the original tissue weight with buffer.

Test drugs are dissolved (10 mg) in 2.5 ml ethanol plus 0.2 1M acetic acid plus 0.3 ml dimethylformamide and sonicated to enhance solution and then diluted to 10 ml with water. The samples are further diluted 1 to 10 with water.

The tritrated spiroperidol ligand has a specific activity of 21 Ci/mmol and is used at a concentration of 0.4 nM.

The incubation mixture consists of 2 ml homogenate, 0.1 ml ligand, and 0.1 ml drug solution or vehicle. The mixture is incubated in a shaking water bath at 30° C. for 30 minutes. After incubation the samples are filtered on Whatman GF/B glass microfibre filters (3.7 cm diameter) using procelain perforated plate funnels and suction flasks operating under house vacuum. The incubation tubes are rinsed once and the filters given a triple 5 ml rinse with cold buffer. The filters are then placed in liquid scintillation counting vials containing 15 ml ACS counting fluid and counted in a liquid scintillation counter.

Samples are run in triplicate and values are expressed using specific binding data. Non-specific binding is determined by adding 1 μM haloperidol to determine the amount of non-displaceable radioactivity. Non-specific binding is subtracted from total bound material to determine specific binding.

D. In vivo spiroperidol Binding Assay

ICR strain mice, weighing about 20 gm, are given the test drugs or vehicle, i.p. or s.c., in 0.10 ml. Drug solutions are in saline, 0.1M citric acid, or 33% propylene glycol. After 1 hour, mice are given 66 micro-Curies (μCi)/kg of $^3$H-spiroperidol (specific activity 21 μCi/mmol) i.v. in 0.10 ml of saline. Four to 6 mice are given each test drug, and 4 of those which are successfully i.v. injected with the label are used for the rest of the experiment. At 3 hours (2 hours after the $^3$H-spiroperidol injection), the mice are sacrificed and the brains rapidly dissected. A section of brain tissue including the striata, septum, most of the olfactory tuberoles, and a small associated portion of the ventral edge of the cortex, is removed to dry ice. The tissues are weighed (usually 60–70 mg) and then dissolved in 1.0 ml of Protosol (New England Nuclear) overnight at about 40° C. The solutions are then neutralized with 80 μl of 6N HCl or 200 μl of 2.4N HCl, 15 ml of ACS counting solution (Amersham) is added, and the samples are counted by liquid scintillation spectroscopy. The amount of bound $^3$H-spiroperiodol, in cpm/mg tissue, is calculated for each test group and compared to the control group using the two-tailed Student's t test.

Of these tests, the in vivo spiroperidol binding assay is the most important indicator of antipsychotic activity. In this test, 1-[3-(5-methyl-4-phenyl-4H-1,2,4-triazol-3-yl)-2-propenyl]-4-phenylpiperazine (Example 3) has been shown to be the most effective. For example, this compound decreased spiroperidol binding in the mouse by approximately 30% at 50 mg/kg. Similarly, among the known triazole anti-allergy compounds disclosed in U.S. Pat. No. 4,338,453, N-methyl-4-phenyl-N-(2-phenylethyl)-4H-1,2,4-triazole-3-propanamine, dihydrochloride has been shown to be the most effective antipsychotic agent. It has an $IC_{50}$ of $10^{-6}$ Molar in the in vivo spiroperidol binding assay in the mouse.

Thus, the compounds of the present invention are useful in humans for the treatment of psychoses, including schizophrenia and acute and chronic psychotic episodes. Some of the compounds of the present invention are also useful for reversing the catalepsy and muscle rigidity or extra pyramidal side effects seen in humans given typical neuroleptics or the nonspecific dopamine receptor blocking type. By "psychosis" is meant any of the psychoses described above in the Background of the Invention.

For a general definition of psychoses and their symptoms, see, Diagnostic and Statistical Manual of Mental Disorders, Third Edition, (DSM-III), American Psychiatric Association, Appendix D, p. 410–424 (1980). As set forth therein, psychoses are classified in sections 290 to 299 of the Ninth Revision of the International Classification of Diseases, World Health Organization, Geneva (1978). An ordinarily skilled physician or psychiatrist who specializes in treating mental disorders of this type will readily determine persons suffering from a psychosis who would benefit from the method of this invention, based on the symptoms set forth, e.g., in DSM-III, supra, at page 188 for schizophrenic disorders, at p. 196 for paranoid disorders, and at page 217 for affective disorders.

An effective but non-toxic quantity of the compound is employed in treatment. The dosage regimen for treating psychoses by the compounds of this invention is selected in accordance with a variety of factors including the type, age, weight, sex, and medical condition of the patient, the severity of the psychosis, the route of administration and the particular compound employed. An ordinarily skilled physician or psychiatrist will readily determine and prescribe the effective amount of the antipsychotic agent to prevent or arrest the progress of the condition. In so proceeding, the physician or psychiatrist could employ relatively low dosages at first, subsequently increasing the dose until a maximum response is obtained.

Initial dosages of the compounds of the invention are ordinarily in the area of 25 mg up to at least 600 mg per day orally, which may be given in a single dose or in multiple doses. When other forms of administration are employed equivalent doses are administered. When dosages beyond 600 mg are employed, care should be taken with each subsequent dose to monitor possible toxic effects.

The compounds of this invention are administered in oral unit dosage forms such as tablets, capsules, pills, powders, or granules. They may also be introduced parenterally, (e.g., subcutaneously, intravenously, or intramuscularly), using forms known to the pharmaceutical art. They also may be administered rectally or vaginally in such forms as suppositories or bougies. In general, the preferred route of administration is oral.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluene-sulfonates and the like. Additionally, the compounds of this invention may be administered in a suitable hydrated form.

One of the compounds of the present invention has also been found to be active in a standard laboratory test which indicates analgesic activity. α,5-Dimethyl-α-[2-[methyl-(2-phenylethyl)amino]ethyl]-4-phenyl-4H-1,2,4-triazole-3-methanol, dihydrochloride (Example 2) has been shown to be effective in these test systems. However, the preferred use of the compounds of this invention is as anti-psychotic agents.

The novel compounds of the present invention (of the Formula I) are prepared by the methods depicted in Chart A. The starting triazoles of the Formula A-3 are prepared by the methods described in U.S. Pat. No. 4,338,453, which is incorporated herein by reference.

Referring to Chart A, the alcohol of the Formula A-1, prepared as described below, which is dissolved in a solvent such as methylene chloride, chloroform or tetrahydrofuran (THF) is treated at −10° to 10° C. with 1.5 equivalents of triethylamine followed by 1.2 equivalents of methanesulfonyl chloride. After stirring for ½ to 2 hours the reaction mixture is quenched in cold aqueous sodium bicarbonate, extracted with methylene chloride or chloroform, dried over sodium sulfate, filtered and concentrated in vacuo to afford the crude mesylate, which is then dissolved in an appropriate solvent such as tetrahydrofuran, 1,2-dimethoxyethane or chloroform, treated with 2.0 equivalents of potassium iodide followed by 2.2 equivalents of an appropriate amine and the mixture is stirred and refluxed for 10–24 hours to yield the Formula A-2 final product.

Alternatively, the triazole of the Formula A-3 is treated with butyl lithium in THF or 1,2-dimethoxy ethane (DME) is hexane mixtures at −78° to −20° C. in order to form the corresponding anion. A β-aminoketone, prepared from the appropriate amine of the formula $HNR_1R_2$ and an alkyl vinyl ketone, is added to a cold solution of the anion in THF and stirred for ½ to 2 hours to yield the formula A-4 compound. (This triazole anion is not stable at temperatures above 0° C.)

The corresponding anion is treated either with a compund of the formula $R_3COCH{=}CH_2$ or 2-cyclohexenone to afford allyl alcohols A-1 and A-6, respectively.

The amino alcohol of the Formula A-4 is treated with 1.5 equivalents of triethyl amine and 1.5 equivalents of acetic anhydride in methylene chloride containing approximately 0.1 equivalents of 4-(dimethylamino)pyridine at −10° C. The mixture is stirred over 24 hours, slowly warming to room temperature to produce the acetate of the Formula A-5. The alcohol of the Formula A-6 is converted to the allyl amine of the Formula A-7 in the same manner as that set forth above for the conversion of the Formula A-1 alcohol to the Formula A-2 product. The alcohol of Formula A-6 may also be first converted to alcohol A-6A following the procedure of Babler, et al., Tet. Lett. 351 (1974).

The allyl amine of the Formula A-7 is then treated with an equivalent of ethereal HCl. Subsequently, the ether is removed and replaced with methanol. Platinum oxide is added and the material is reduced with hydrogen in a Parr apparatus at 50 psi initial pressure, to yield the Formula A-8 product.

The known compounds employed in the method of this invention are prepared as described in U.S. Pat. No. 4,338,453.

Certain compounds of the present invention are preferred. Thus, compounds of the formula II wherein n is zero are preferred. More preferred are compounds of the formula II wherein n is zero, $R_4$ is hydrogen or methyl, and $W_2$ is trans—$CH{=}CH—CH_2NR_1R_2$, —$C(CH_3)(OR_{14})—CH_2—CH_2NR_1R_2$, or a substituent of the formula III. Most preferred are compounds of this latter class wherein $R_5$ is phenyl or ortho, meta, or para-halo phenyl, and $W_2$ is trans—$CH{=}CH—CH_2NR_1R_2$ or a substituent of the Formula III (wherein the dotted line represents a double bond) and wherein —$NR_1R_2$ is —$N(CH_3)—CH_2—CH_2$—phenyl or a substituent of the formula VI or $W_2$ is a substituent of the formula III and the dotted line represents a double bond. Thus 1-[3-(5-methyl-4-phenyl-4H-1,2,4-triazol-3-yl)-2-propenyl]-4-phenyl-piperazine (Example 3) is the most preferred compound of this invention.

DESCRIPTION OF THE PREFERRED EMBODIMENTS

The present invention is seen more fully by the Examples given below.

Preparation 1

1-(5-Methyl-4-phenyl-4H-1,2,4-triazol-3-yl)-2-cyclohexen-1-ol

Refer to Chart A (conversion of A-3 to A-6).

A flame dried 1 liter, 3-neck round bottomed flask fitted with a 500 ml addition funnel, rubber dam, nitrogen inlet and magnetic stirrer is charged with 64.1 ml of n-butyllithium (102 mmol) in 150 ml of THF and cooled to −78° C. in a dry-ice acetone bath. 4-phenyl-3-methyl-4H-1,2,4-triazole (15.9 g, 100 mmol) dissolved in 350 ml of THF is slowly added dropwise to the well-stirred solution of n-butyllithium while the temperature is maintained at −78° C. The addition takes 1.3 hours. A solid precipitates. The mixture is treated with 100 ml of additional THF, warmed to approximately 0° for 5 min, recooled to −78° C. and treated with an additional 10 ml of 1.6M n-butyllithium (16 mmol). To the mixture stirred at −78° C. is added 11.53 g (120 mmol) of 2-cyclohexenone dissolved in 100 ml THF. The reaction flask is then placed in a water bath at room temperature for several hours. The mixture is quenched in cold aqueous sodium hydroxide (10%), extracted with methanol/chloroform mixtures, dried over sodium sulfate and concentrated in vacuo. The product is crystallized from methanol/ethyl acetate mixtures in several crops to afford crystals of the allylic alcohol in 38.3% yield, having mp of 181°–183° C. An additional 9.1% of product is obtained following chromatography of the crude residue: IR (nujol) spectrum reveals peaks at 3150, 1644, 1537, 1496, 1375, 1172, and 999 $cm^{-1}$ and the UV spectrum (95% EtOH) λmax shows peaks at 251 nm (ε184), 256 nm (ε237), 259 nm (ε209), and 266 nm (ε138). The NMR ($CDCl_3$, δ) shows peaks at 7.15–7.60, 5.70, 3.67, 2.15, and 1.55–2.25. The mass spectrum reveals ions at m/e 255, 238, 236, 160, and 118.

Anal. Calcd. for $C_{15}H_1/N_3O$, mw 255.31: C, 70.56; H, 6.71; N, 16.46. Found: C, 70.43; H, 6.72; N, 16.34.

Example 1

4-Chloro-N-methyl-N-[3-(5-methyl-4-phenyl-4H-1,2,4-triazol-3-yl)-2-cyclohexen-1-yl]benzeneethanamine, and its (E)-2-butenedioate (1:1), ethyl acetate solvate (2:1), hydrate (Formula I: $R_4$ is methyl, $R_5$ is phenyl, n is zero, $W_1$ is the Formula III substituent and the dotted line represents a double bond, $NR_1R_1$ is —$N(CH_3)—CH_2—CH_2R_{25}$, wherein $R_{25}$ is p-chloro-phenyl)

Refer to Chart A (conversion of A-6 to A-7).

The mesylate is prepared by treating a solution of 2.55 g (10.0 mmol) of starting material (Preparation 1), 2.06 ml (15.0 mmol) of triethylamine dissolved in 40 ml of methylene chloride with a solution of 1.72 g (15.0 mmol) of methanesulfonyl chloride dissolved in 15 ml of methylene chloride. The mesylate is isolated from aqueous sodium carbonate and dissolved in 40 ml of THF containing 3.39 g (20.0 mmol) p-chloro-N-methyl-β-phenethylamine and 3.32 g (20.0 mmol) of potassium iodide. The mixture is refluxed for 15 hours, cooled, quenched in cold aqueous 10% sodium hydroxide, extracted with chloroform, dried over sodium sulfate and concentrated in vacuo. The resulting oil is chromatographed over 300 g of silica gel by eluting with 3 liters (l) of 5% methanol/95% chloroform mixtures.

Fractions 35–44 contain a semi-solid which crystallizes from ethyl acetate hexane mixtures.

Fractions 45–58 contain 1.117 g of oil which crystallizes as a fumaric acid salt from methanol/ethyl acetate mixtures to give 0.868 g of prisms of the titled compound, with a mp of 157°–163°. The IR (nujol) spectrum yields a peak of 1458 $cm^{-1}$. The UV spectrum (95% ethanol) reveals a shoulder a 207 nm (ϵ40,200). The mass spectrum reveals ions at m/e 406.1902, 238, 116 and 98.

Anal. Calcd. for $C_{24}H_{2}$/$ClN.C_4H_4O_4.\frac{1}{2}C_4H_8O_2.H_2O$: $C_{30}H_{3}$/$ClN_4O_6$, mw 585.09; C, 61.58; H, 6.38; N, 9.58; Cl, 6.06. Found: C, 61.77; H, 6.05; N, 9.41; Cl, 6.18.

Example 2

α5-Dimethyl-α-(2-(methyl-(2-phenylethy)amino)ethyl-4-phenyl-4H-1,2,4-triazole-3-methanol (Formula I: $R_4$ is methyl, $R_5$ is phenyl, n is zero, $W_1$ is —C($CH_3$)(OH)—$CH_2CH_2NR_1R_2$, —$NR_1R_2$ is —N($CH_3$)—$CH_2CH_2$—$R_{25}$ and $R_{25}$ is phenyl)

Refer to Chart A (conversion of Formula A-3 to A-4).

6.37 g (4.00 mmols) of 4-phenyl-3-methyl-4H-1,2,4-triazole is dissolved in 15 ml of tetrahydrofuran (THF) cooled to −78° C. in a dry ice/acetone bath and is treated with 2.63 ml of 1.6M n-butyllithium. The mixture is stirred for 10 min at −78° C. and then treated with 0.859 g (414 mmols) of the amino ketone corresponding to the titled product dissolved in 5 ml of THF. This mixture is stirred at −78° C. for one half hr and then allowed to warm to ambient temperature. After one hr the reaction is quenched in cold aqueous sodium hydroxide, extracted with chloroform, and dried over sodium sulfate. The mixture is concentrated in vacuo to yield an oil. After chromatography, crystals are obtained having a melting point of 202°–205° C. and percentages of carbon:hydrogen:nitrogen:chlorine (hereinafter C:H:N:Cl ratio) of 60.11:6.84:12.73:16.21, respectively (calcd 60.41:6.91:12.81:16.21).

Preparation 2

α-Vinyl-5-methyl-4-phenyl-4H-1,2,4-triazole-3-methanol

Refer to Chart A (conversion of Formula A-3 to A-1).

15.9 g (100 mmols) of 4-phenyl-3-methyl-4H-1,2,4-triazole and 400 ml THF are added to a one 1, 3-neck round bottom flask which is cooled to −78° C. This mixture is treated with 64.1 ml of n-butyllithium in hexane. After one third of the n-butyllithium is added, 100 ml of tetrahydrofuran is added. The remaining n-butyllithium is added, and the mixture is stirred for ¼ hr. 6.168 g of acrolein in 100 ml THF is added and the mixture is warmed to ambient temperature. Additional 20 ml of n-butyllithium and 4.0 g of acrolein is added. The mixture is concentrated in vacuo to yield a colorless solid. This mixture is dissolved in methanol and 100 ml of 1N hydrochloric acid. The mixture is concentrated in vacuo and again dissolved in chloroform. The mixture is chromatographed on 1 kg of silica gel by eluting with 3 l of 5% methanol/95% chloroform and 5 l of 8% methanol/92% chloroform, one l fractions are collected. Fractions 6 and 7 yield 7.69 g of the titled product, having a melted point of 167°–171° C. The C:H:N ratio is 66.85:6.20:19.60 (calcd 66.95:6.09:19.53).

Example 3

(E)-1-[3-(5-methyl-4-phenyl-4H-1,2,4-triazol-3-yl)-2-propenyl]-4-phenyl-piperazine (Formula I: $R_4$ is methyl, $R_5$ is phenyl, n is zero, $W_1$ is trans—CH═CH—$CH_2NR_1R_2$, —$NR_1R_2$ is the formula VI substituent wherein $R_{25}$ is phenyl)

Refer to Chart A (conversion of A-1 to A-2).

1.075 g (5.00 mmols) of the compound of Preparation 2 is dissolved in 20 ml of methylene chloride and treated with triethylamine and cooled to 0°–5° C. This mixture is treated with a solution of 0.5 ml (6.4 mmols) of methanesulfonyl chloride in 7.5 ml of methylene chloride. The mixture is stirred for ¼ hr and quenched in cold aqueous sodium carbonate. The mixture is extracted with methylene chloride and dried over sodium sulfate. The mixture is filtered and concentrated in vacuo, and dissolved in 20 ml of tetrahydrofuran. The solution is then treated with potassium iodide and N-phenylpiperazine and heated to reflux for 6 hr. The reaction is quenched with cold aqueous sodium carbonate and extracted with chloroform. The chloroform solution is then dried over sodium sulfate and concentrated in vacuo. After chromatography, the titled crystals are obtained having a melting point of 171°–172° C. and a C:H:N ratio of 73.37:7.12:19.67 (calcd 73.50:7.01:19.49).

Example 4

(E)-3-methyl-5-[3-[methyl(2-phenylethyl)amino]-1-propenyl]-4-phenyl-4H-1,2,4-triazole (Formula I: $R_4$ is methyl, $R_5$ is phenyl, n is zero, $W_1$ is trans—CH═CH—$CH_2NR_1R_2$, $NR_1R_2$ is —N($CH_3$)—$CH_2CH_2R_{25}$, and $R_{25}$ is phenyl)

Refer to Chart A (conversion of A-1 to A-2).

Employing the procedure of Example 3, and using the appropriate amine, the titled crystals are obtained having a melting point of 79°–81.5° C. The analytical sample has mp 81.5–83 and a C:H:N ratio of 75.79:7.24:16.77 (calcd 75.87:7.27:16.86).

Preparation 3

1-(5-Methyl-4-phenyl-4H-1,2,4-triazol-3-yl)-2-cyclohexen-1-ol

Refer to Chart A (conversion of A-3 to A-6).

A flame-dried one l 3-neck round bottomed flask equipped with a 500 ml addition funnel, a nitrogen inlet, and magnetic stirring bar is charged with 64.1 ml of n-butyllithium in 150 ml of THF and cooled to −78° C. in a dry ice acetone bath. 15.9 g (100 mmols) of the compound 4-phenyl-3-methyl-4H-1,2,4-triazole, is dissolved in 350 ml of THF, is slowly added drowpwise to the solution while stirring. Addition is accomplished over 1.3 hr. An additional 10 ml of n-butyllithium is added along with 100 ml of THF. 11.53 g of 2-cyclohexenone and 100 ml of THF is added to the solution which is maintained at −78° C. The mixture is brought to room temperature and stirred for 15 min until the temperature reached approximately 10° C. The reaction is quenched with aqueous sodium hydroxide and extracted with chloroform/methanol and dried over sodium sulfate. The mixture is worked up as previously described to yield the titled crystals having a melting point of 181°–183° C. and a C:H:N ratio of 70.43:6.72:16.34 (calcd 70.56:6.71:16.46).

Preparation 4

3-(5-methyl-4-phenyl-4H-1,2,4-triazol-3-yl)-2-cyclohexene-1-ol

Refer to Chart A (conversion of A-6 to A-6A).

Following the procedure described in Babler, Tet. Lett. 351 (1974) 2.55 g (10.0 mmols) of the alcohol prepared in Preparation 3 is dissolved in 25 ml of acetic acid and is added to a solution of 10 ml of acetic anhydride and p-toluene sulfonic acid hydrate (PTSOH) (1.80 g, 9.45 mmols) dissolved in 25 ml of acetic acid. After 20 min the reaction is quenched in sodium carbonate and extracted with chloroform and dried over sodium sulfate. The mixture is concentrated in vacuo. An additional 1.200 g of PTSOH is added and the mixture is stirred overnight. The reaction is quenched with sodium carbonate and extracted with chloroform. Finally the mixture is dried over sodium sulfate and concentrated in vacuo. The crude acetate is dissolved in 20 ml of methanol and to it is added 11.09 g (168 mmols) of 4.0N potassium hydroxide over a 10 min period. The mixture is refluxed for 4 hr and stirred at room temperature overnight. The reaction is quenched with cold aqueous sodium hydroxide and extracted with chloroform. Finally the mixture is dried over sodium sulfate and concentrated in vacuo to yield an oil. This oil is crystallized from methanol/ethyl acetate to give 1.53 g of titled crystals having a melting point of 169°-173° C. The C:H:N ratio is 70.18:6.69:16.40 (calcd 70.56:6.71:16.46).

Example 5

N-methyl-N-[3-(5-methyl-4-phenyl-4H-1,2,4-triazol-3-yl)-2-cyclohexen-1-yl]-benzenethanamine (Formula I: $R_4$ is methyl, $R_5$ is phenyl, n is zero, $W_1$ is the formula III substituent, the dotted line is a double bond, $NR_1R_2$ is —N($CH_3$)—$CH_2CH_2R_{25}$, and $R_{25}$ is phenyl)

Refer to Chart A (conversion of A-6 to A-7).

0.638 g (2.5 mmol) of the alcohol prepared in Preparation 4 is dissolved in 10 ml methylene chloride and cooled to 0° C. in an ice bath and treated with 0.52 ml (3.75 mmol) of triethylamine and 0.461 g (4.02 mmol) of methenesulfonyl chloride in 4.0 ml of methylene chloride. The mixture is stirred for 1 hr and warmed to ambient temperature. The reaction is quenched with cold aqueous sodium carbonate, extracted with methylene chloride, dried over sodium sulfate, and concentrated in vacuo. This material is dissolved in 12 ml of THF containing 0.68 g of N-methyl-$\beta$-phenethylamine and 0.83 g (5.00 mmol) of potassium iodide is added. The mixture is heated to reflux for 20 hr after which the reaction is quenched with cold aqueous sodium hydroxide. The mixture is chromatographed over 150 g of silica gel eluting with 5% methanol/95% chloroform containing 5 ml of ammonium hydroxide per liter. 20 ml fractions were collected after discarding the first 100 ml forecut. Fractions 18-30 are concentrated in vacuo to yield 0.372 g of an oil which is combined with a separate 0.173 g prepared in the same manner. This was treated with 1 equivalent (0.167) g of fumaric acid and crystallized from methanol/ethyl acetate to give 551 mg of prisms having a melting point of 159°-161° C. and a C:H:N ratio of 64.15:7.02:8.75 (calcd 63.90:7.26:8.77).

Example 6

(E)-4-chloro-N-methyl-N-[3-(5-methyl-4-phenyl-4H-1,2,4-triazol-3-yl)-2-propenyl]benzeneethanamine (Formula I: $R_4$ is methyl, $R_5$ is phenyl, n is zero, $W_1$ is —CH=CH—$CH_2NR_1R_2$, $NR_1R_2$ is —N($CH_3$)$CH_2CH_2R_{25}$, and $R_{25}$ is p-chlorophenyl)

Refer to Chart A (conversion of A-1 to A-2).

Using the compound of Preparation 2 and the procedures described in Example 3, and employing the appropriate amine starting material, the titled crystals are obtained having a melting point of 99°-101° C. and a C:H:N:Cl ratio of 68.87:6.53:15.06:9.60 (calcd 68.74:6.32:15.27:9.66).

Example 7

4-chloro-N-methyl-N-[3-(5-methyl-4-phenyl-4H-1,2,4-triazol-3-yl)-2-cyclohexen-1-yl]benzeneethanamine (Formula I: $R_4$ is methyl, $R_5$ is phenyl, n is zero, $W_1$ is the Formula III substituent, the dotted line represents a double bond, $NR_1R_2$ is N($CH_3$)$CH_2CH_2R_{25}$ and $R_{25}$ is p-chlorophenyl)

Refer to Chart A (conversion of Formula A-6 to A-7).

Using the compound of Preparation 4 and the procedure described in Example 5, and employing the appropriate amine starting materials, the titled crystals are obtained having a melting point of 157°-163° C. and a C:H:N:Cl ratio of 61.77:6.05:9.41:6.18 (calcd 61.58:6.38:9.58:6.06).

Example 8

Cis-N-methyl-3-(5-methyl-4-phenyl-4H-1,2,4-triazol-3-yl)-N-(2-phenylethyl)cyclohexanamine and Trans-N-methyl-3-(5-methyl-4-phenyl-4H-1,2,4-triazol-3-yl)-N-(2-phenylethyl)-cyclohexanamine (Formula I: $R_4$ is methyl, $R_5$ is phenyl, n is zero, $W_1$ is the Formula III substituent, the dotted line represents a single bond, and $NR_1R_2$ is —N($CH_3$)—$CH_2$—$CH_2R_{25}$ and $R_{25}$ is phenyl)

1.31 g (3.52 mmols) of the compound of Example 5 is dissolved in 6 ml of methanol and treated with ethereal hydrochloric acid and concentrated to an oil in vacuo and is then dissolved in 50 ml of methanol and heated with 0.4 g of $PtO_2$ and reduced at 45 psi in a Parr apparatus. After chromatography, the two titled isomers are obtained: The less polar isomer had N—$CH_2CH_2$—Phenyl signals in the NMR spectrum at 2.59, N—$CH_3$/triazole $CH_3$ at 2.20 and 2.12 g. The more polar isomer had N—$CH_2CH_2$—phenyl signals at 2.65 with N—$CH_3$/triazole singlets at 2.29 and 2.22$\delta$.

Example 9

Following the procedures described in U.S. Pat. No. 4,338,453, the following compounds are prepared for use in the method of this invention:

5-Methyl-4-phenyl-N-(2-phenylethyl)-4H-1,2,4-triazole-3-ethanamine, dihydrochloride, monohydrate;

N,5-Dimethyl-4-phenyl-N-(2-phenylethyl)-4H-1,2,4-triazole-3-ethanamine, monohydrobromide;

N-methyl-4-phenyl-N-(2-phenylethyl)-4H-1,2,4-triazole-3-propanamine;

$\alpha$-[[[2-(3,4-dichlorophenyl)ethyl]methylamino]methyl]-5-methyl-4-phenyl-4H-1,2,4-triazole-3-methanol;

N-[2-(4-chlorophenyl)ethyl]-N-methyl-4-phenyl-4H-1,2,4-triazole-3-propanamine, dihydrochloride;

N-[2-(3,4-dichlorophenyl)ethyl]-N-methyl-4-phenyl-4H-1,2,4-triazole-3-propanamine, bis-(4-methylbenzenesulfonate);

$\alpha$-[[4-(4-chlorophenyl)-1-piperazinyl]methyl]-5-methyl-4-phenyl-4-1,2,4-triazole-3-methanol;

5-[3-[methyl(2-phenylethyl)amino]propyl]-α, 4-diphenyl-4H-1,2,4-triazole-3-methanol;

α-[[[2-(4-chlorophenyl)ethyl]methylamino]methyl]-5-methyl-4-phenyl-4H-1,2,4-triazole-3-methanol;

4-phenyl-N-(2-phenylethyl)-4H-1,2,4-triazole-3-propanamine, dihydrochloride;

α-[2-[[2-(4-Chlorophenyl)ethyl[methylamino]ethyl]-5-(n-propyl)-4-phenyl-4H-1,2,4-triazole-3-methanol;

N-[2-(4-chlorophenyl)ethyl]-3-ethoxy-N-methyl-3-[4-phenyl-5-(n-propyl)-4H-1,2,4-triazol-3-yl]propanea-mine;

N-[2-(4-Chlorophenyl)ethyl]-3-ethyl-N-methyl-3-[4-phenyl-5-(n-propyl)-4H-1,2,4-triazole-3-yl]propanamine;

α-[[[2-(3,4-Dichlorophenyl)ethyl]methylamino]methyl]-5-methyl-4-phenyl-4H-1,2,4-triazole-3-methanol, acetate ester; and 5-Mercapto-4-phenyl-α-(4-phenyl-1-piperazinyl)methyl-4H-1,2,4-triazole-3-methanol, acetate ester.

FORMULA

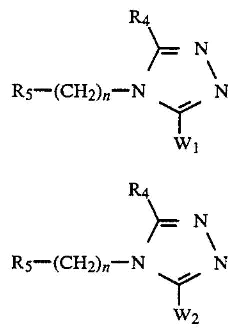

-continued

FORMULA

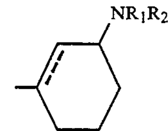

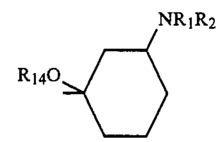

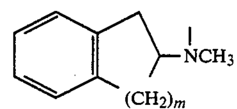

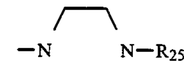

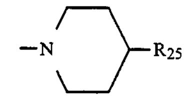

CHART A

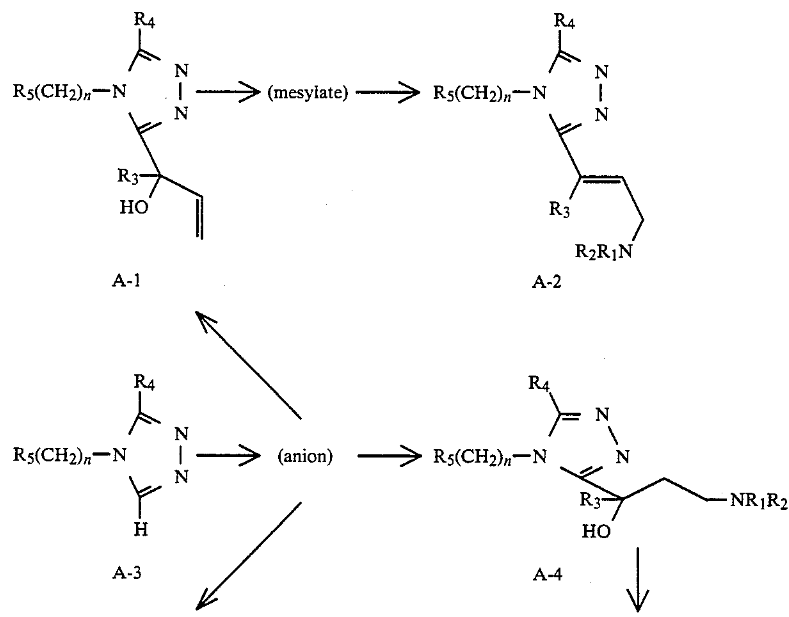

-continued

CHART A

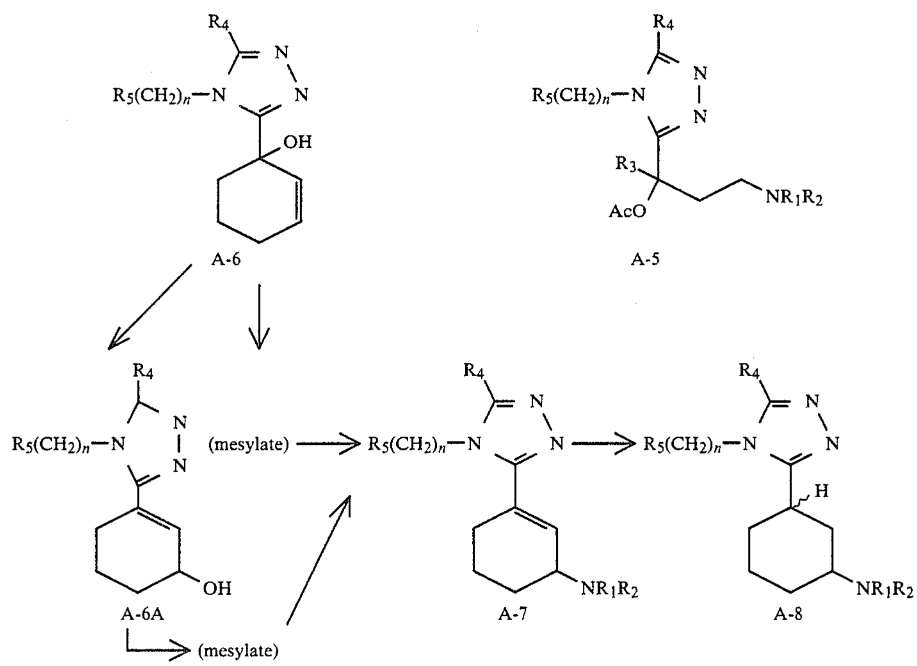

I claim:

1. A compound of the Formula I,

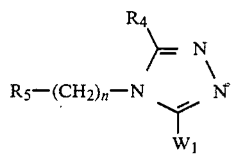

I or an enantiomer or stereoisomer thereof, wherein $P_4$ is (a) hydrogen, (b) $(C_1-C_3)$ alkyl, (c) $—CH_2OH$, (d) $—CH_2OCOCH_3$, (e) $—S(O)_qCH_3$, (f) $—SCH_2CH_3$, or (g) $—R_{15}$;

wherein $R_5$, $R_{15}$, and $R_{25}$ are the same or different and are (a) phenyl substituted by zero to 2 chloro, fluoro, bromo, alkyl of from one to 3 carbon atoms, nitro, or alkoxy of from one to 3 carbon atoms, or (b) phenyl substituted by one trifluoromethyl and zero to one of the previous phenyl substituents;

wherein $W_1$ is (a) cis—$C(R_3)=CH—CH_2NR_1R_2$, (b) trans—$C(R_3)=CH—CH_2NR_1R_2$, (c) $—C(CH_3)(OR_{14})—CH_2—CH_2NR_1R_2$, (d) a substituent of the Formula III, or

III

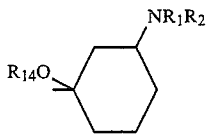

(e) a substituent of the Formula IV;

IV

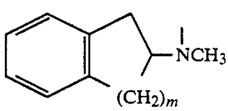

wherein $—NR_1R_2$ is (a) $—N(CH_3)—CH_2(CH_2)_m—R_{25}$, (b) $—NH—CH_2(CH_2)_mR_{25}$, (c) a substituent of the Formula V,

V

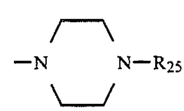

(d) a substituent of the Formula VI,

VI $$—N\langle\ \rangle N—R_{25}$$

(e) a substituent of the Formula VII, or

VII

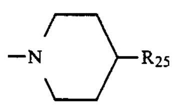

(f) —$N(CH_3)$—$(CH_2)_3$—$CH(R_{51})_2$;

wherein $R_{14}$ is
- (a) hydrogen,
- (b) —$COCH_3$, or
- (c) —$COCH_2CH_3$;

wherein $R_{51}$ is
- (a) phenyl,
- (b) p-fluorophenyl, or
- (c) p-chlorophenyl;

wherein $R_3$ is
- (a) hydrogen or
- (b) methyl;

wherein the dotted line represents a single or double bond;

wherein m is an integer of from one to 2, inclusive;

wherein n is an integer of from zero to 3, inclusive; and wherein q is an integer of from zero to 2, inclusive; or a pharmacologically acceptable acid addition salt; or solvate or hydrate thereof.

2. A compound of claim 1, wherein n is zero.

3. A compound of claim 2, wherein $R_4$ is hydrogen or methyl and $W_1$ is trans—CH═CH—$CH_2NR_1R_2$, —$C(CH_3)(OR_{14})$—$CH_2$—$NR_1R_2$, or a substituent of the formula III

III

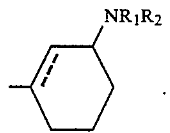

4. A compound of claim 3, wherein $R_5$ is phenyl or ortho-, meta-, or para-halo phenyl, and $W_1$ is trans—CH═CH—$CH_2NR_1R_2$ wherein —$NR_1R_2$ is —$N(CH_3)$—$CH_2$—$CH_2$—phenyl or a substituent of the formula VI

IV

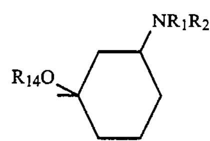

or $W_1$ is a substituent of the formula III

III

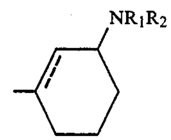

and the dotted line represents a double bond.

5. A compound of claim 4 selected from the group consisting of 4-chloro-N-methyl-N-[3-(5-methyl-4-phenyl-4H-1,2,4-triazol-3-yl)-2-cyclohexen-1-yl]benzeneethanamine, and its (E)-2-butenedioate (1:1), ethyl acetate solvate (2:1), hydrate;

α, 5-Dimethyl-α-[2-[methyl-(2-phenylethyl)amino]ethyl]-4-phenyl-4H-1,2,4-triazole-3-methanol;

1-[3-(5-methyl-4-phenyl-4H-1,2,4-triazol-3-yl)-2-propenyl]-4-phenylpiperazine;

(E)-3-methyl-5-[3-([methyl(2-phenylethyl)amino]-1-propenyl]-4-phenyl-4H-1,2,4-triazole;

N-methyl-N-[3-(5-methyl-4-phenyl-4H-1,2,4-triazol-3-yl)-2-cyclohexen-1-yl]benzeneethanamine;

(E)-4-chloro-N-methyl-N-[3-(5-methyl-4-phenyl-4H-1,2,4-triazol-3-yl)-2-propenyl]benzeneethanamine;

4-chloro-N-methyl-N-[3-(5-methyl-4-phenyl-4H-1,2,4-triazol-3-yl)-2-cyclohexen-1-yl]benzeneethanamine;

Cis-N-methyl-3-(5-methyl-4-phenyl-4H-1,2,4-triazol-3-yl)-N-(2-phenylethyl)cyclohexamine and Trans-N-methyl-3-(5-methyl-4-phenyl-4H-1,2,4-triazol-3-yl)-N-(2-phenylethyl)cyclohexanamine.

* * * * *

UNITED STATES PATENT OFFICE
CERTIFICATE OF CORRECTION

Patent No. 4,577,020 Dated 18 March 1986

Inventor(s) Martin Gall

It is certified that error appears in the above-identified patent and that said Letters Patent are hereby corrected as shown below:

Column 9, line 20, "yl-4-phenyl-" should read -- yl)-4-phenyl- --.

Column 13, line 7, ")ethyl[methylamino]" should read -- )ethyl]methylamino] --.

Column 17, line 31, "$(OR_{14})-CH_2-NR_1R_2$, or" should read -- $(OR_{14})-CH_2-CH_2NR_1R_2$, or --.

Signed and Sealed this

Twenty-first Day of October, 1986

[SEAL]

*Attest:*

DONALD J. QUIGG

*Attesting Officer*

*Commissioner of Patents and Trademarks*